United States Patent
Maruyama et al.

(10) Patent No.: US 10,426,319 B2
(45) Date of Patent: Oct. 1, 2019

(54) IMAGING DEVICE, ATTACHMENT FOR IMAGING DEVICE AND IMAGE PROCESSING METHOD

(71) Applicant: RF CO., LTD., Nagano-shi, Nagano (JP)

(72) Inventors: Jiro Maruyama, Nagano (JP); Akio Koyanagi, Nagano (JP)

(73) Assignee: RF CO., LTD., Nagano-Shi, Nagano (JP)

(*) Notice: Subject to any disclaimer, the term of this patent is extended or adjusted under 35 U.S.C. 154(b) by 90 days.

(21) Appl. No.: 15/865,931

(22) Filed: Jan. 9, 2018

(65) Prior Publication Data
US 2018/0199795 A1    Jul. 19, 2018

(30) Foreign Application Priority Data

Jan. 19, 2017 (JP) ................................. 2017-007256

(51) Int. Cl.
| | |
|---|---|
| *G06K 9/00* | (2006.01) |
| *A61B 1/00* | (2006.01) |
| *A61B 1/07* | (2006.01) |
| *A61B 1/06* | (2006.01) |
| *H04N 5/225* | (2006.01) |
| *A61B 1/005* | (2006.01) |

(52) U.S. Cl.
CPC ........ *A61B 1/0005* (2013.01); *A61B 1/00009* (2013.01); *A61B 1/0052* (2013.01); *A61B 1/0057* (2013.01); *A61B 1/0607* (2013.01); *A61B 1/0669* (2013.01); *A61B 1/0684* (2013.01); *A61B 1/07* (2013.01); *H04N 5/2256* (2013.01); *H04N 2005/2255* (2013.01)

(58) Field of Classification Search
CPC . A61B 1/0005; A61B 1/00009; A61B 1/0052; A61B 1/0057; A61B 1/0607; A61B 1/0669; A61B 1/0684; A61B 1/07; H04N 5/2256; H05N 2005/2255
See application file for complete search history.

(56) References Cited

U.S. PATENT DOCUMENTS

| | | | | |
|---|---|---|---|---|
| 2011/0141140 | A1* | 6/2011 | Duhamel | G06T 7/0012 345/629 |
| 2015/0305610 | A1* | 10/2015 | Giraldo Cadavid | A61B 1/267 600/560 |

FOREIGN PATENT DOCUMENTS

JP       2009-089955 A      4/2009

OTHER PUBLICATIONS

Dunn, Stanley M., Richard L. Keizer, and Jongdaw Yu. "Measuring the area and volume of the human body with structured light." IEEE Transactions on Systems, Man, and Cybernetics 19.6 (1989): 1350-1364. (Year: 1989).*

* cited by examiner

*Primary Examiner* — Jonathan S Lee
(74) *Attorney, Agent, or Firm* — Manabu Kanesaka

(57) ABSTRACT

A imaging device includes: a spotlight emitting unit configured to emit two parallel spotlights; an imaging element configured to capture a measurement frame image having two spot areas irradiated with the spotlights and a plurality of first frame images which do not have the two spot areas, during capturing a moving image; and a controller configured to generate a grid image having a plurality of grid lines arranged at intervals set on the basis of the distance between the two spot areas in the measurement frame image, generate a plurality of second frame images by superimposing the grid image on the first frame images, and display the second frame images on a display unit.

6 Claims, 10 Drawing Sheets

IMAGING DEVICE, ATTACHMENT FOR IMAGING DEVICE AND IMAGE PROCESSING METHOD

CROSS-REFERENCE TO RELATED APPLICATION

This application is based upon and claims the benefit of priority from Japanese Patent Application No. 2017-007256, filed Jan. 19, 2017, the entire contents of which are incorporated herein by reference.

FIELD

The present invention described herein relates to an imaging device, and in particular, to an image processing technique for displaying grid lines in a moving image.

BACKGROUND

Conventionally, imaging devices such as endoscopes for imaging the inside of pipes and the like are known (for example, Patent Literature 1). For example, the endoscope has an imaging unit at a tip end portion of a cable to be inserted into pipes and the like. Upon operating an operation unit by a user, the tip end portion of the cable is directed at a desired direction, so that the imaging direction of the imaging unit is changed to the desired direction. Images captured by the endoscope are displayed on a display unit.

An object can be seen in an image captured by the imaging device, but the size of the object is difficult to recognize. For example, since the distance between the imaging unit and the object changes in accordance with an insertion state and the imaging direction of the cable, the size of the object is difficult to grasp from the captured image. Furthermore, the imaging device changes the size of the imaged object in the captured image by zooming in or out the object by an imaging optical system, and therefore the size of the object is difficult to grasp from the captured image.

SUMMARY OF THE INVENTION

It is an object of the present invention to provide an imaging device and an image processing method that facilitate grasping the size of an object.

An imaging device according to the present invention includes: a spotlight emitting unit configured to emit two parallel spotlights; an imaging element configured to capture a measurement frame image having two spot areas irradiated with the spotlights and a plurality of first frame images which do not have the two spot areas, during capturing a moving image; and a controller configured to generate a grid image having a plurality of grid lines arranged at intervals set on the basis of the distance between the two spot areas in the measurement frame image, generate a plurality of second frame images by superimposing the grid image on the first frame images, and display the second frame images on a display unit.

An image processing method according to the present invention includes: setting intervals of grid lines on the basis of the distance of two spot areas in a measurement frame image, out of a measurement frame image having the two spot areas irradiated with two parallel spotlights and a plurality of first frame images which do not have the two spot areas that are imaged during capturing a moving image; generating a grid image having the grid lines arranged at the intervals; and generating a plurality of second frame images by superimposing the grid image on the first frame images.

According to the present invention, the two spotlights for forming the two spot areas in the measurement frame image are in parallel with each other. Thus, even if, for example, the distance between an imaging unit and an object changes, the actual distance between the spot areas does not change. In other words, even if the distance between the imaging unit and the object changes, the ratio between the size of the imaged object and the distance between the spot areas is constant in the measurement frame image.

According to the present invention, the intervals of the grid lines are set on the basis of the distance between the spot areas in the measurement frame image. Thus, according to the present invention, the ratio between the interval of the grid lines and the size of the imaged object is constant even in the second frame image, irrespective of the distance between the imaging unit and the object.

Therefore, according to the present invention, a comparison between the interval of the grid lines and the imaged object facilitates grasping the size of the object, irrespective of the distance between the imaging unit and the object. The present invention also allows the measurement of the concrete size of the object on the basis of the intervals of the grid lines.

In the present invention, the controller may generate the grid image in which the grid lines obliquely intersect each side of the second frame image.

According to the present invention, since the grid lines obliquely intersect each side of the second frame image, the grid lines are easily visible.

In the present invention, the spotlight emitting unit may be one end of an optical fiber on the other end of which light is incident from a light source.

According to the present invention, since the optical fibers convert the light from the light sources into parallel light and emit the parallel light as the spotlights, the spotlights have good parallelism. Therefore, the present invention allows keeping the actual distance between the spot areas at a certain distance with high accuracy, thus providing high accuracy in the intervals of the grid lines.

In the present invention, the imaging device may further include a cable having a tip end portion the direction of which is changeable, and an imaging unit provided in the tip end portion. The imaging unit may include the imaging element, a lens configured to condense light into the imaging element, two of the spotlight emitting units, and two illumination light emitting units configured to emit illumination light to illuminate an object to be imaged. The two spotlight emitting units and the two illumination light emitting units may be alternately arranged at regular intervals in a circumferential direction about an optical axis of the lens.

According to the present invention, the two spotlight emitting units and the two illumination light emitting units are alternately arranged at the regular intervals in the circumferential direction about the optical axis of the lens. Thus, the present invention prevents that the illumination light is biased to any one of spotlight irradiation positions. In other words, since the two spotlights are applied in uniform brightness distribution in an imaging area, it is possible to easily recognize the two spot areas in the measurement frame image. Accordingly, the distance between the two spot areas is easily calculated.

An attachment according to the present invention is attached to an imaging device, and is configured to emit parallel two spotlights. During capturing a moving image, the imaging device captures a measurement frame image having two spot areas irradiated with the spotlights from the attachment and a plurality of first frame images which do not have the two spot areas, generates a grid image having a plurality of grid lines arranged at intervals set on the basis of the distance between the two spot areas in the measurement frame image, and generates a plurality of second frame images by superimposing the grid image on the first frame images.

According to the present invention, by attaching the attachment to the imaging device, just as with the above-described imaging device, the imaging device having the attachment can capture the measurement frame image and the first frame images. The imaging device can generate the grid image on the basis of the measurement frame image, and generate the second frame images by superimposing the grid image on the first frame images. Therefore, it is possible to easily grasp the size of the object by a comparison between the interval of the grid lines and the imaged object in the second frame images.

DETAILED DESCRIPTION

Figure 1:
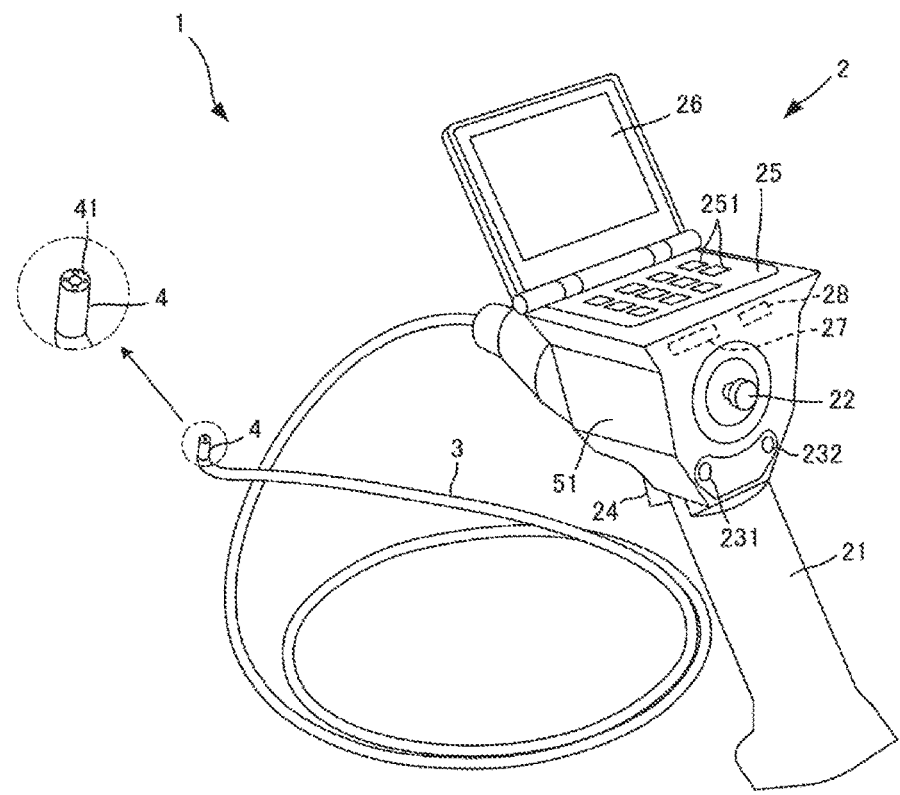
FIG. 1 is a perspective view of an endoscope.

Embodiments will be described below with reference to the drawings. FIG. 1 is a perspective view of an endoscope 1. The endoscope 1 includes a main body 2, a cable 3, and an imaging unit 4 disposed at a tip end portion of the cable 3. The imaging unit 4 includes a tip end surface 41 that is disposed at a distal end of the cable 3 in an axial direction. The imaging unit 4 images an imaging area opposite the tip end surface 41.

The main body 2 includes a grip 21, an operation portion 22, buttons 231 and 232, a trigger 24, an operation panel 25, a display unit 26, a controller 27, and a memory 28.

The grip 21 is a portion that a user grips with his/her right hand or the like.

The operation portion 22 is a lever. Tilting the operation portion 22 changes the direction of the tip end portion of the cable 3 and thus changes the imaging direction of the imaging unit 4. The operation portion 22, the buttons 231 and 232, and the trigger 24 are disposed in such positions that the user can operate each of the components 22, 231, 232, and 24 while holding the grip 21 with his/her right hand.

The operation panel 25 includes a plurality of buttons 251 for inputting settings and the like of the endoscope 1.

The display unit 26 displays an image captured by the imaging unit 4, setting information of the endoscope 1, and notification information for the user. Note that the display unit 26 may not be provided in the endoscope 1. In this case, the endoscope 1 may be connected to an external display unit, and the image captured by the imaging unit 4 may be sent from the endoscope 1 to the external display unit.

The controller 27 is a CPU (central processing unit) to control the entire endoscope 1. The controller 27 loads programs from the memory 28, and executes various types of processing. The controller 27 starts capturing a moving image upon a press of the button 231, and stops capturing the moving image upon a press of the button 232. The controller 27 stores the captured moving image in the memory 28. Upon depressing the trigger 24, the controller 27 captures a still image and stores the still image in the memory 28.

Figure 2:
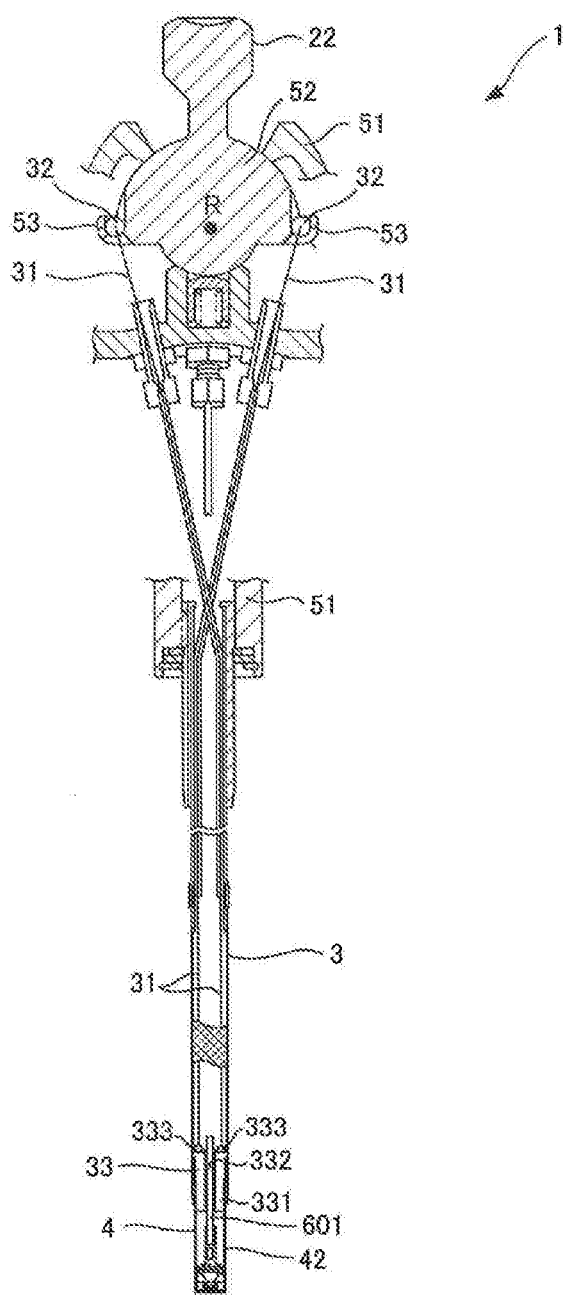
FIG. 2 is a cross-sectional view of the endoscope.

FIG. 2 is a sectional view of the endoscope 1, showing a mechanism for changing the imaging direction. This mechanism is the same as that described in JP2009-089955. The mechanism will be described below in brief. Note that, FIG. 2 shows a part of an exterior member 51, which is an exterior of the main body 2.

The operation portion 22 is erected on an operation portion main body 52, which is mostly contained in the exterior member 51. The operation portion main body 52 is turnable in three dimensions about the center R of turning. A side surface of the operation portion main body 52 is provided with four holder portions 53 at equal intervals in a circumferential direction. The holder portions 53 hold balls 32 each of which is connected to an end of a wire 31. Each of the four wires 31 extends through the inside of the exterior member 51 to the tip end portion of the cable 3, while one end of each wire 31 is supported by the holder portion 53.

The exterior member 51 secures one end of the cable 3. The cable 3 is tubular and elastically deformable in shape. A column-shaped fixation member 33 is secured inside the tip end portion of the cable 3.

The fixation member 33 has a reduced diameter portion 331 at its distal end side. A proximal end of a cylindrical case member 42 of the imaging unit 4 is inserted into a gap between an outer peripheral surface of the reduced diameter portion 331 and an inner peripheral surface of the cable 3. The imaging unit 4 is thereby secured at the tip end portion of the cable 3.

The fixation member 33 has a hole 332 penetrating through a central axis. A signal line 601 extends through the hole 332. The signal line 601 is connected to the imaging unit 4 at one end, and is connected to the controller 27 at the other end. The controller 27 supplies electric power to the imaging unit 4 through the signal line 601, to drive the imaging unit 4. Captured images outputted from the imaging unit 4 are inputted to the controller 27 through the signal line 601.

The fixation member 33 has four attachment portions 333 at its proximal end. The attachment portions 333 are arranged around the hole 332 at regular intervals in a circumferential direction. FIG. 2 shows only two of the attachment portions 333. Each of the four wires 31 is supported by the holder portion 53 at one end, and is secured to the attachment portion 333 at the other end.

Figure 3:
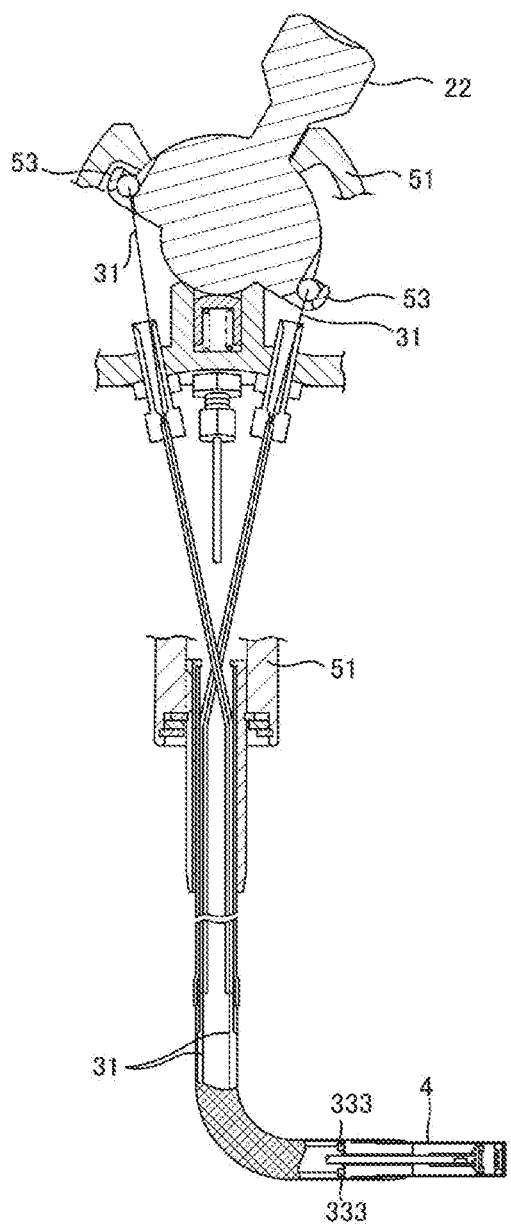
FIG. 3 is a cross-sectional view of the endoscope in a state of changing the direction of a tip end portion of a cable.

As shown in FIG. 2, when the cable 3 extends straight, the two wires 31 that are symmetric with respect to the central axis of the cable 3 intersect inside the exterior member 51. Thus, for example, when the operation portion 22 is turned to the right in FIG. 2, the left holder portion 53 ascends in FIG. 2, and the right attachment portion 333 is pulled upward in FIG. 2. As a result, as shown in FIG. 3, the tip end portion of the cable 3 is directed to the right, and therefore the imaging direction of the imaging unit 4 changes to the right. In this embodiment, as described above, the imaging direction is changeable in accordance with the turning direction of the operation portion 22.

Figure 4:
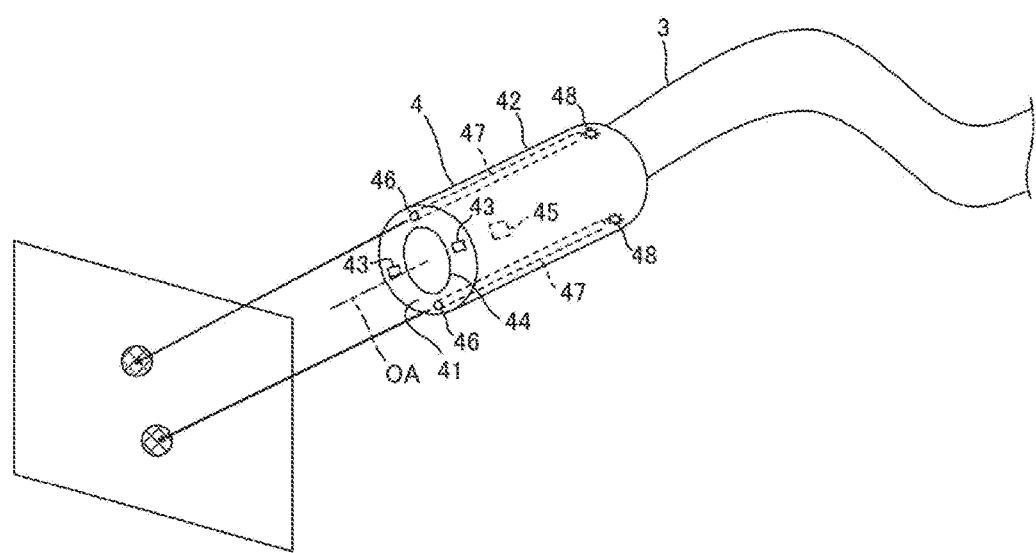
FIG. 4 is a schematic view of an imaging unit.

FIG. 4 is a schematic view of the imaging unit 4. The imaging unit 4 includes the case member 42, illumination light emitting units 43, a lens 44, an imaging element 45, spotlight emitting units 46, optical fibers 47, and light sources 48.

The case member 42 is cylindrical in shape, as described above. The lens 44, the illumination light emitting units 43, and the spotlight emitting units 46 are exposed from the tip end surface 41 of the case member 42. The case member 42 contains the respective components 43 to 48. In the case member 42, a not-shown securing member secures each of the components 43 to 48.

The two illumination light emitting units 43 are each a light source such as an LED (light emitting diode) for emitting white light. When imaging is performed in a dark environment and the like, the illumination light emitting units 43 emit the white light to illuminate an imaging area. The two illumination light emitting units 43 are positioned point-symmetrically with respect to an optical axis OA of the lens 44.

The optical axis OA of the lens 44 coincides with the central axis of the case member 42. The lens 44 condenses light from an object into the imaging element 45. This embodiment uses a single-focus optical system, as an optical system between the lens 44 and the imaging element 45. This optical system preferably has a focusing function. A zooming optical system may be used as the optical system.

The imaging element 45 is, for example, a CCD (charge coupled device) for capturing an image of an object.

There are two spotlight emitting units 46. The two spotlight emitting units 46 are positioned point-symmetrically with respect to the optical axis OA of the lens 44. The two spotlight emitting units 46 and the two illumination light emitting units 43 are alternately arranged at regular intervals in a circumferential direction about the optical axis OA of the lens 44. Each spotlight emitting unit 46 emits a spotlight, i.e., a laser beam and projects the spotlight onto the inside of the imaging area. Each spotlight emitting unit 46 emits the spotlight along the direction of the optical axis OA of the lens 44.

Each of the two optical fibers 47 emits the spotlight from its one end. The one end of the optical fiber 47 constitutes the spotlight emitting unit 46.

The two light sources 48 are each constituted of, for example, an LED. Each light source 48 emits light to allow the light to be incident on the other end of the optical fiber 47.

Figure 5A:
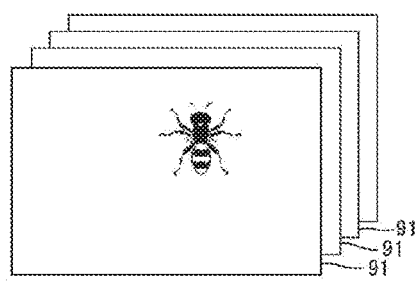
FIGS. 5(A) to 5(F) are drawings of captured images and the like in each step of image processing.
Figure 5B:
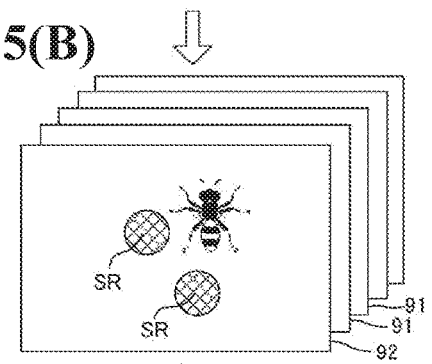
Figure 5E:
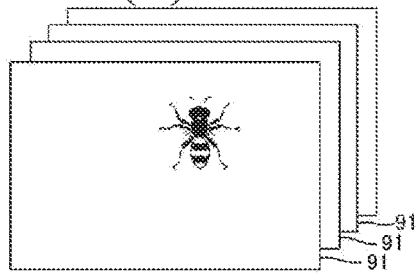
Figure 5C:
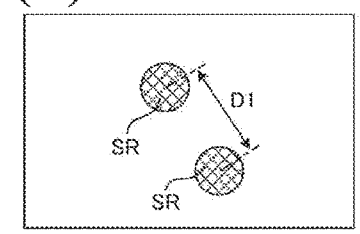

Image processing by the controller 27 will be described below with reference to FIGS. 5(A) to 5(F) and 6. When starting capturing a moving image upon a press of the button 231, operation is performed as shown in FIG. 6. The operation of FIG. 6 is performed within a certain time period (for example, 1 second), and is repeated whenever the certain time period elapses. By capturing a moving image within the certain time period, a plurality of frame images (first frame images) 91 are captured as shown in FIG. 5(A). When capturing the moving image, a frame rate is, for example, 30 FPS (frames per second). The controller 27 is on standby, until specific timing arrives (NO in step S1). The specific timing is timing when an arbitrary frame image 91, out of the moving image (frame images 91) captured within the certain time period, is captured. The specific timing may be, for example, timing when the first frame image 91 is captured within the certain time period.

Upon arriving at the specific timing (YES in step S1), the controller 27 turns on the two light sources 48, so that the spotlight emitting units 46 project spotlights onto two positions inside an imaging area, respectively (step S2). Thus, as shown in FIG. 5(B), a measurement frame image 92 that has spot areas SR irradiated with the two spotlights is obtained. The number of the obtained measurement frame images may be one or two or more, depending on an emission time of the spotlights.

The controller 27 calculates the distance D1 between the two spot areas SR on the basis of the measurement frame image 92 (step S3). The distance D1 may be, as shown in FIG. 5(C), the distance between the center of one of the spot areas SR and the center of the other spot area SR. When a plurality of measurement frame images 92 are obtained, the distance D1 may be calculated on the basis of one of the measurement frame images 92.

Figure 5D:
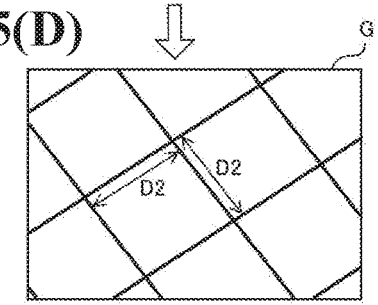
Figure 6:
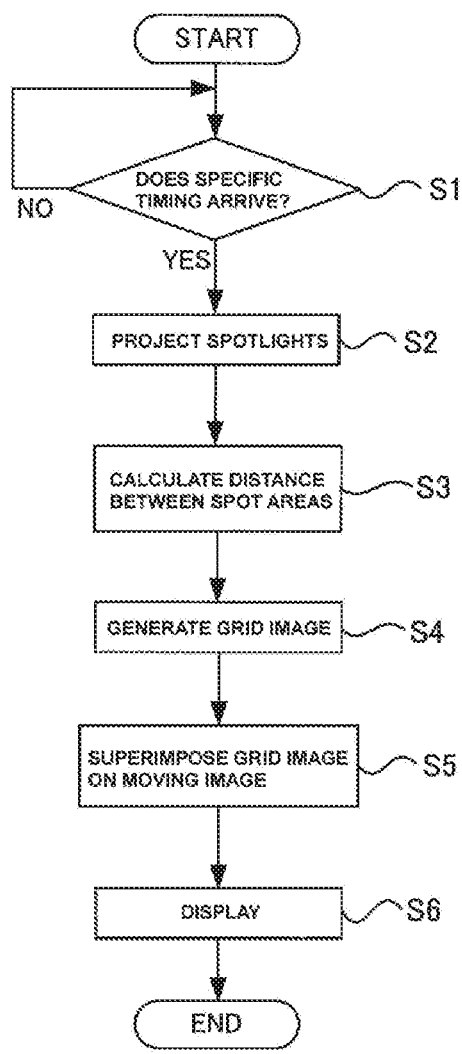
FIG. 6 is a flowchart of the image processing.

The controller 27 generates a grid image G, as shown in FIG. 5(D), on the basis of the distance D1 (step S4). In the grid image G, a plurality of grid lines extending in two directions are formed, and a plurality of square grids formed by the grid lines are arranged in the two directions. The grid lines are inclined with respect to each side of the grid image G. The crossing two grid lines intersect at right angles. The controller 27 sets a length (intervals of the grid lines) D2 of one side of each grid of the grid image G on the basis of the distance D1. To be more specific, the controller 27 sets a length that is proportional to the distance D1, as the length D2. The length D2 may be equal to the distance D1, or may be a length in which the distance D1 is multiplied by a certain coefficient (a value larger than 0).

Figure 5F:
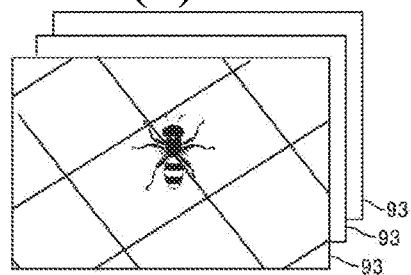

The controller 27 superimposes the grid image G on each of the frame images 91 captured as the moving image, as shown in FIG. 5(E), to generate frame images (second frame images) 93 having the grid lines, as shown in FIG. 5(F) (step S5). The frame images 93 constitute a moving image having the grid lines. The captured moving image includes the measurement frame image 92, but the measurement frame image 92 is removed from the generated moving image having the grid lines.

The controller 27 displays the moving image having the grid lines (frame images 93) on the display unit 26 (step S6).

The controller 27 captures the frame images 91 in a state of turning off the light sources 48, until the next specific timing. Thus, as shown in FIG. 5(E), the moving image captured during this time does not include the measurement frame image 92, but includes only the frame images 91.

In the next specific timing, the controller 27 turns on the two light sources 48 and captures a measurement frame image 92 again, and updates the grid image G on the basis of the measurement frame image 92. Note that, since the measurement frame image 92 is removed from the generated moving image having the grid lines, it is required to prepare a frame image 93 alternative to the measurement frame image 92, for the purpose of displaying the moving image at a predetermined frame rate. Therefore, for example, the controller 27 may use a frame image 93 that is generated from the frame image 91 immediately before or after the measurement frame image 92, as the frame image 93 alternative to the measurement frame image 92. In other words, the controller 27 displays the same two frame images 93 in series. Therefore, this embodiment prevents a lack in the frame images 93, when displaying the moving image having the grid lines on the display unit 26.

Depending on a turn-on duration and turn-on timing of the light sources 48, there is conceivable a case where the spot areas SR are seen in a plurality of frame images 91, in other words, measurement frame images 92 continue. In this case, the controller 27 generates a grid image G using any one of the measurement frame images 92. Just as described above, the controller 27 removes the measurement frame images 92, and prepares alternative frame images 93 the number of which is the same as that of the removed measurement frame images 92.

The controller 27 can store the moving image having the grid lines in the memory 28. The controller 27 can also store a moving image constituted of only the plurality of frame images 91, as shown in FIG. 5(E), in the memory 28.

(Effects)

In this embodiment, since the two spotlights are emitted in parallel from the two spotlight emitting units 46, even if the distance between the imaging unit 4 and the object changes, the actual distance between the spot areas SR is constant. Thus, the size of the imaged object and the distance D1 between the spot areas SR change at the same ratio in the measurement frame image 92 depending on a change in the distance between the imaging unit 4 and the object. For example, when the distance between the imaging unit 4 and the object increases, the size of the imaged object and the distance D1 between the spot areas SR decreases at the same ratio in the measurement frame image 92.

In other words, the ratio between the size of the imaged object and the distance D1 between the spot areas SR is constant in the measurement frame image 92, irrespective of the distance between the imaging unit 4 and the object. In the frame images 93, since the length D2 of one side of the grid image G is set on the basis of the distance D1 between the spot areas SR, the ratio between the length D2 and the size of the imaged object is constant irrespective of the distance between the imaging unit 4 and the object.

Therefore, when the length D2 of one side of the grid image G is smaller than the object, even if the distance between the imaging unit 4 and the object changes, the length D2 remains smaller than the size of the imaged object in the frame images 93. The ratio of the length D2 to the size of the object does not change.

Therefore, this embodiment facilitates grasping the size of the object by comparison between the length D2 of one side of the grid image G and the imaged object, irrespective of the distance between the imaging unit 4 and the object. This embodiment also allows the measurement of the concrete size of the object on the basis of the length D2.

According to this embodiment, the grid image G is updated whenever emitting the spotlights. Thus, even if the distance between the imaging unit 4 and the object changes during the capture of the moving image, the grid image G can be generated in accordance with the change. During the capture of the moving image, it is possible to continue grasping the size of the object, with reference to the length D2.

According to this embodiment, since the controller 27 inclines the grid lines such that each side of the grid lines obliquely intersects each side of the second frame image 93, each side of the grid lines is easily visible.

According to this embodiment, since the optical fibers 47 convert diffusion light emitted from the light sources 48 into parallel light, the spotlights emitted from the two spotlight emitting units 46 have good parallelism. Therefore, as described above, this embodiment allows keeping the actual distance between the spot areas SR at a certain distance with high accuracy, even when changing the distance between the imaging unit 4 and the object, thus providing high accuracy in the grid image G.

In this embodiment, the two spotlight emitting units 46 and the two illumination light emitting units 43 are alternately arranged at the regular intervals in the circumferential direction around the optical axis OA of the lens 44. Thus, this embodiment prevents that the illumination light from the illumination light emitting units 43 is biased to any one of the spotlight irradiation positions. Thus, since the two spotlights are projected in uniform brightness distribution in the imaging area, it is possible to easily recognize the two spot areas SR in the measurement frame image 92. Accordingly, the distance D1 is easily calculated on the basis of the two spot areas SR.

Modification Examples

Figure 7A:
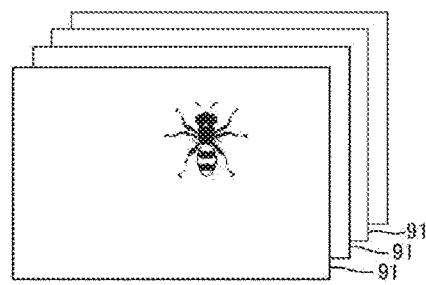
FIGS. 7(A) to 7(F) are drawings of captured images and the like in each step of image processing according to a modification example.
Figure 7B:
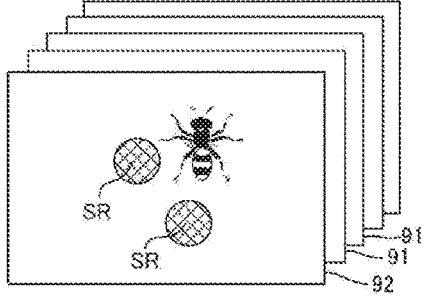
Figure 7E:
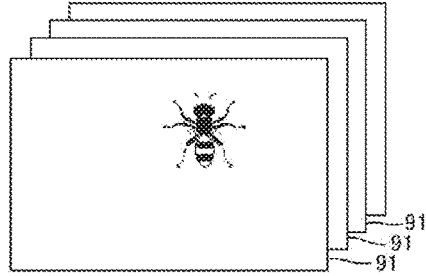
Figure 7C:
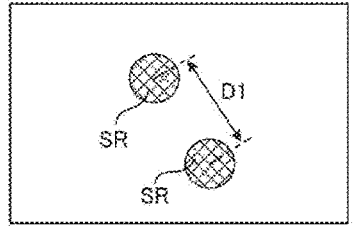
Figure 7D:
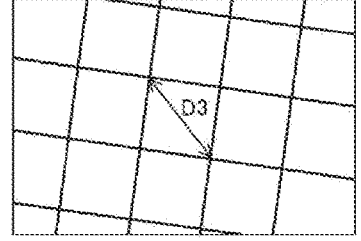
Figure 7F:
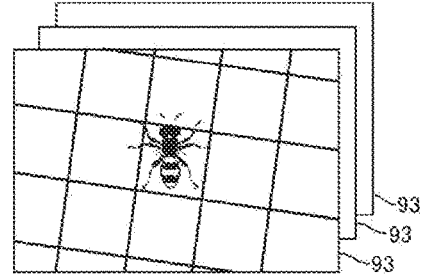

In the aforementioned embodiment, as shown in FIG. 5(D), the controller 27 sets the length D2 of one side of the grid in the grid image G on the basis of the distance D1 between the spot areas SR in the measurement frame image 92. However, as shown in FIG. 7(D), the controller 27 may set the length D3 of a diagonal line of a grid in a grid image G on the basis of the distance D1, and generate a grid image G. Since the grids are square in the grid image G, the length of one side of the grid is determined on the basis of the length D3. Grid lines can be generated with reference to the diagonal line of the grid.

Figure 8I:
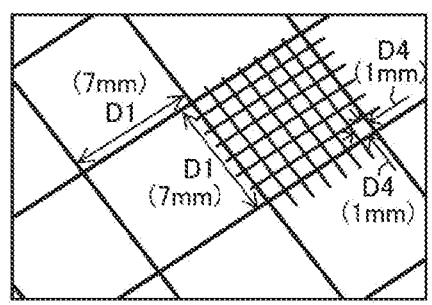
FIGS. 8(I) and 8(II) are drawings of grid images according to another modification example.
Figure 8:
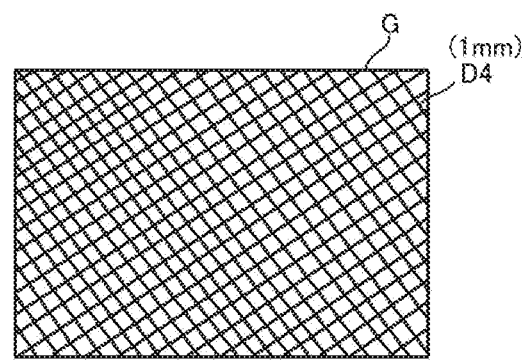

FIGS. 8(I) and 8(II) are drawings of a grid image G according to a modification example. FIG. 8(I) is a drawing showing the length D4 of one side of a grid, relative to the distance D1. FIG. 8(II) is a drawing showing the grid image G in which the length of one side of a grid is set at D4.

The controller 27 may set the length D4 of one side of the grid in the grid image G at a length (see FIG. 8(I)) into which the distance D1 between the spot areas SR of the measurement frame image 92 is evenly divided by a certain division number. In this embodiment, the distance between the two spotlight emitting units 46 is set at 7 mm. In other words, the distance D1 between the spot areas SR in the measurement frame image 92 is 7 mm. The controller 27 sets a length D4 (1 mm) that the distance D1 (7 mm) between the spot areas SR is divided into seven, as the length D4 of one side of the grid in the grid image G.

Figure 9I:
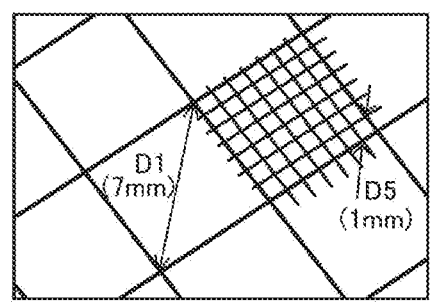
FIGS. 9(I) and 9(II) are drawings of grid images according to yet another modification example.
Figure 9:
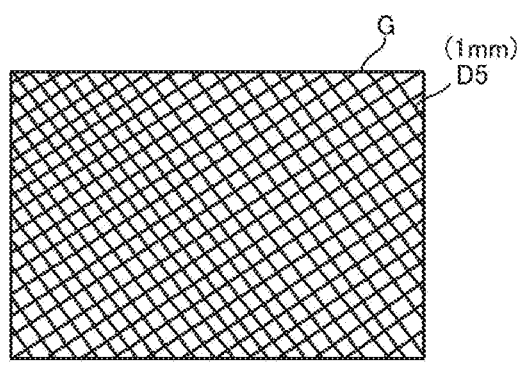

FIGS. 9(I) and 9(II) are drawings of a grid image G according to another modification example. FIG. 9(I) is a drawing showing the length D5 of a diagonal line of a grid, relative to the distance D1. FIG. 9(II) is a drawing showing the grid image G in which the length of the diagonal line of the grid is set at D5.

Just as with processing of FIGS. 8(I) and 8(II), the controller 27 may set the length D5 of the diagonal line of the grid in the grid image G at a length (see FIG. 9(I)) into which the distance D1 between the spot areas SR of the measurement frame image 92 is evenly divided by a certain division number. In this embodiment, the distance between the two spotlight emitting units 46 is set at 7 mm. In other words, the distance D1 between the spot areas SR in the measurement frame image 92 is 7 mm. The controller 27 sets a length D5 (1 mm) that the distance D1 (7 mm) between the spot areas SR is divided into seven, as the length D5 of the diagonal line of the grid in the grid image G.

In the embodiment and the modification examples, the controller 27 makes the grids into the shape of a square in the grid image G, but may make the grids into the shape of a rhombus.

The endoscope 1 itself may not generate the grid image G and superimpose the grid image G on the frame images 91. A computer wirelessly or wiredly connected to the endoscope 1 may obtain a measurement frame image 92 from the endoscope 1, and generate a grid image G on the basis of the measurement frame image 92. The computer may generate frame images 93 by superimposing the grid image C on frame images 91. The computer may display the frame images 93 (in other words, a moving image having grid lines) on a display unit connected to the computer.

Figure 10:
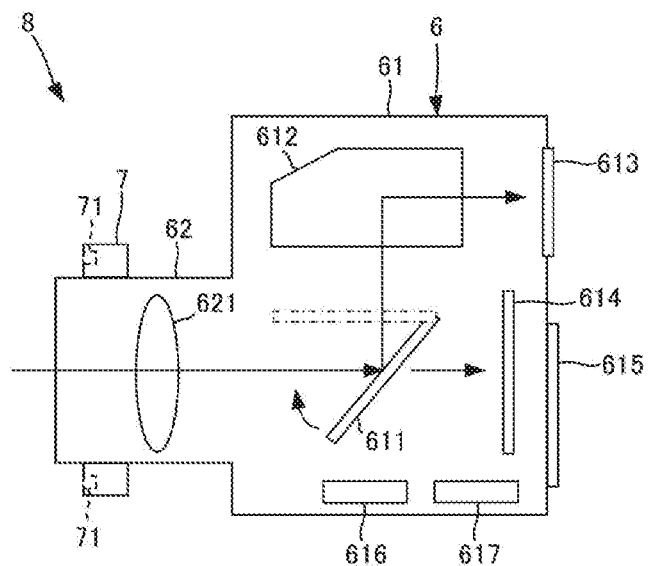
FIG. 10 is a drawing of a single-lens reflex camera.

FIG. 10 is a drawing of a camera system 8.

In the above-described embodiment, the spotlight emitting units 46 are provided in the endoscope 1. In this modification example, spotlight emitting units 71 are provided in the camera system 8.

The camera system 8 includes a camera body 6 and an attachment 7.

The camera body 6 includes a main body 61 and a lens barrel 62. The lens barrel 62, which holds a lens 621, is detachable from and attachable to the main body 61.

The main body 61 includes a mirror 611, a penta-prism 612, a finder 613, an imaging element 614, a display unit 615, a controller 616, and a memory 617.

Before a press of a not-shown shutter button, the mirror 611 reflects light having passed through the lens 621 to the side of the finder 613. The penta-prism 612 reflects the light reflected from the mirror 611 to the finder 613. A user sees an image having passed through the imaging lens 621 in the finder 613. Upon pressing the shutter button, a not-shown drive mechanism lifts the mirror 611, so that the light having passed through the lens 621 is incident on the imaging element 614. Note that, in the camera system 8 shown in FIG. 10, the mirror 611, the penta-prism 612, and the finder 613 may be omitted.

The attachment 7 is detachable from and attachable to the lens barrel 62. The attachment 7, which may be ring-shaped, is fitted on the lens barrel 62 in a detachable manner. The attachment 7 includes a pair of spotlight emitting units 71, and a power supply such as a not-shown battery for supplying electric power to the spotlight emitting units 71. The spotlight emitting units 71 are disposed across an optical axis of the lens 621 point-symmetrically with respect to the optical axis. The spotlight emitting units 71 have the same operations and functions as the spotlight emitting units 46, and emit two spotlights parallel with the optical axis of the lens 621. The spotlight emitting unit 71 may be an end of an optical fiber that emits light from a light source, or may be a light source itself such as an LED for emitting a laser beam. The spotlight emitting units 71 projects the two spotlights to the inside of an imaging area of the camera body 6.

To capture a moving image, the controller 616 makes the imaging element 614 capture a measurement frame image 92 having spot areas SR irradiated with the spotlights and a plurality of first frame images 91 having no spot area. The controller 616 sets intervals of grid lines on the basis of the distance D1 between the spot areas SR in the measurement frame image 92, as with steps S3 to S6 described above. The controller 616 generates a grid image G having a plurality of grid lines arranged at the intervals, and superimposes the grid image G on the first frame images 91 to generate second frame images 93. The controller 616 displays a moving image constituted of the second frame images 93 on the display unit 615.

Note that, according to the modification example, since the spotlight emitting units 71 are provided in the attachment 7, the spotlight emitting units 71 may be attached to the camera body 6 in a detachable manner. However, the spotlight emitting units 71 may be directly contained in the main body 61 or the lens barrel 62, instead of the attachment 7. In the above-described modification example, a controller contained in the attachment 7 controls the turn-on of the spotlight emitting units 71 independently of the controller 616, but the controller 616 of the camera body 6 may controls the turn-on of the spotlight emitting units 71 instead.

Figure 11:
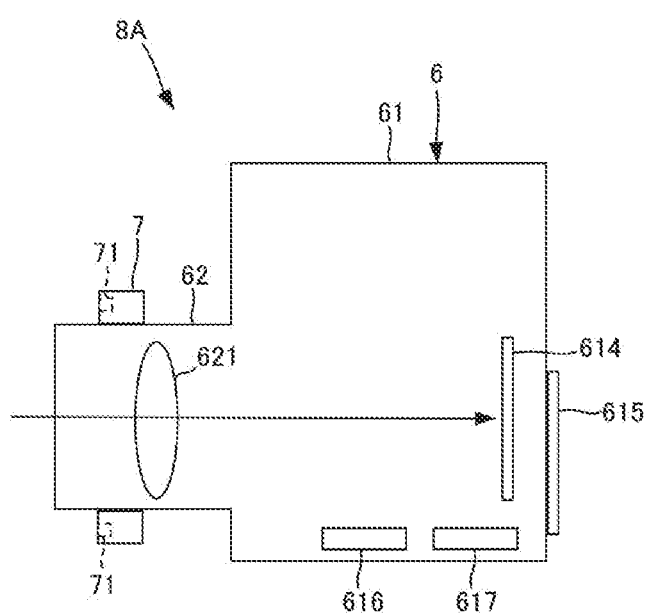
FIG. 11 is a drawing of a compact camera.

FIG. 11 is a drawing of a camera 8A.

The attachment 7 having the spotlight emitting units 71 may be attached to a camera body 6 of the camera 8A.

In the camera 8A, a lens barrel 62 for supporting a lens 621 and a main body 61 that contains an imaging element 614 for receiving light having passed through the lens 621 are integrally secured. The main body 61 contains a controller 616 and a memory 617, while supporting a display unit 615. In contrast to the camera system 8, the camera 8A does not have a mirror 611 to reflect an image having passed through the lens 621 to the side of the finder 613. In the camera 8A, as described above, the lens barrel 62 and the main body 61 are integrally secured.

Also in this modification example, the spotlight emitting units 71 projects two spotlights to the inside of an imaging area of the camera body 6. The controller 616 captures a measurement frame image 92 having spot areas SR and a plurality of first frame images 91 having no spot area SR. The controller 616 superimposes a grid image G, which is generated on the basis of the measurement frame image 92, on the first frame images 91, in order to generate a plurality of second frame images 93. The controller 616 displays a moving image constituted of the second frame images 93 on the display unit 615.

Note that, the spotlight emitting units 71 may be contained in the camera body 6. A controller contained in the attachment 7 controls the turn-on of the spotlight emitting units 71 independently of the controller 616, but the controller 616 of the camera body 6 may controls the turn-on of the spotlight emitting units 71 instead.

What is claimed is:

1. An imaging device comprising:
    a spotlight emitting unit configured to emit two parallel spotlights;
    an imaging element configured to capture a measurement frame image having two spot areas irradiated with the spotlights and a plurality of first frame images which do not have the two spot areas, during capturing a moving image; and
    a controller configured to generate a grid image having a plurality of grid lines arranged at intervals set on a basis of a distance between the two spot areas in the measurement frame image, generate a plurality of second frame images by superimposing the grid image on the first frame images, and display the second frame images on a display unit.

2. The imaging device according to claim 1, wherein the controller generates the grid image in which the grid lines obliquely intersect each side of the second frame image.

3. The imaging device according to claim 1, wherein the spotlight emitting unit is one end of an optical fiber on the other end of which light is incident from a light source.

4. The imaging device according to claim 1, comprising:
    a cable having a tip end portion a direction of which is changeable; and
    an imaging unit provided in the tip end portion, and wherein
    the imaging unit includes the imaging element,
a lens configured to condense light into the imaging element,
two of the spotlight emitting units, and
two illumination light emitting units configured to emit illumination light to illuminate an object to be imaged, and the two spotlight emitting units and the two illumination light emitting units are alternately arranged at regular intervals in a circumferential direction about an optical axis of the lens.

5. An attachment to be attached to an imaging device, the attachment being configured to emit parallel two spotlights, wherein during capturing a moving image, the imaging device captures a measurement frame image having two spot areas irradiated with the spotlights from the attachment and a plurality of first frame images which do not have the two spot areas, generates a grid image having a plurality of grid lines arranged at intervals set on a basis of a distance between the two spot areas in the measurement frame image, and generates a plurality of second frame images by superimposing the grid image on the first frame images.

6. An image processing method comprising:

setting intervals of grid lines on a basis of a distance of two spot areas in a measurement frame image, out of a measurement frame image having the two spot areas irradiated with two parallel spotlights and a plurality of first frame images which do not have the two spot areas that are imaged during capturing a moving image;

generating a grid image having the grid lines arranged at the intervals; and generating a plurality of second frame images by superimposing the grid image on the first frame images.

* * * * *